United States Patent
Marshall et al.

(10) Patent No.: US 7,850,684 B2
(45) Date of Patent: Dec. 14, 2010

(54) SURGICAL INSTRUMENT

(75) Inventors: Mark G. Marshall, Winnersh (GB); Francis Amoah, Reading (GB); Frank D'Amelio, Santa Barbara, CA (US)

(73) Assignee: Gyrus Medical Limited, Cardiff (GB)

( * ) Notice: Subject to any disclaimer, the term of this patent is extended or adjusted under 35 U.S.C. 154(b) by 916 days.

(21) Appl. No.: 11/717,180

(22) Filed: Mar. 13, 2007

(65) Prior Publication Data

US 2007/0219549 A1 Sep. 20, 2007

(30) Foreign Application Priority Data

Mar. 16, 2006 (GB) ................................ 0605348.2

(51) Int. Cl.
*A61B 18/14* (2006.01)
(52) U.S. Cl. ............................... 606/39; 606/34; 606/48
(58) Field of Classification Search .................. 606/34, 606/38–37
See application file for complete search history.

(56) References Cited

U.S. PATENT DOCUMENTS

| | | | | |
|---|---|---|---|---|
| 4,311,143 | A * | 1/1982 | Komiya | 606/47 |
| 5,971,980 | A * | 10/1999 | Sherman | 606/34 |
| 6,022,347 | A * | 2/2000 | Lindenmeier et al. | 606/38 |
| 6,212,426 | B1 | 4/2001 | Swanson | |
| 6,228,081 | B1 | 5/2001 | Goble | |
| 2002/0049442 | A1 * | 4/2002 | Roberts et al. | 606/50 |
| 2002/0052599 | A1 | 5/2002 | Goble | |
| 2002/0165531 | A1 * | 11/2002 | Goble | 606/40 |
| 2004/0102770 | A1 | 5/2004 | Goble | |
| 2004/0260279 | A1 | 12/2004 | Goble et al. | |
| 2005/0070892 | A1 | 3/2005 | Ciarrocca | |
| 2005/0096644 | A1 | 5/2005 | Hall et al. | |
| 2007/0066971 | A1 * | 3/2007 | Podhajsky | 606/34 |

FOREIGN PATENT DOCUMENTS

| | | |
|---|---|---|
| EP | 0 754 437 A2 | 1/1997 |
| GB | 2414185 A | 11/2005 |
| WO | WO 97/24995 | 7/1997 |
| WO | WO 2005/112806 | 12/2005 |
| WO | WO 2005/117735 A | 12/2005 |

OTHER PUBLICATIONS

Search Report in Application No. GB0605348.2 (filed Mar. 16, 2006) (Date of Search: Jul. 12, 2006).
Search Report in corresponding Application No. PCT/GB2007/000874, mailed May 7, 2007.

* cited by examiner

*Primary Examiner*—Lee S Cohen
*Assistant Examiner*—Jaymi Della
(74) *Attorney, Agent, or Firm*—Nixon & Vanderhye P.C.

(57) ABSTRACT

A device for morcellating tissue within a body cavity of a patient comprises a stationary tube (8) having a distal end portion (12), and a bipolar electrosurgical electrode assembly (13) located at the distal end of the tube. The electrosurgical electrode assembly (13) comprises first and second electrodes (14, 16) separated by an insulating member (15), the bipolar electrosurgical electrode assembly extending around the circumference of the distal edge of the tube (8). When a pulsed electrosurgical cutting voltage is applied to the electrode assembly (13) and relative movement is initiated between the tube (8) and the tissue, a core of severed tissue is formed within the tube such that it can be removed from the body cavity of the patient. Temperature sensors (60) can be used to measure the temperature at the distal end of the tube (8), and to vary the duty cycle of the pulsed cutting voltage.

33 Claims, 11 Drawing Sheets

SURGICAL INSTRUMENT

CROSS REFERENCE TO RELATED APPLICATIONS

This application claims priority from UK Application No. GB0605348.2, filed Mar. 16, 2006.

BACKGROUND OF THE INVENTION

This invention relates to a bipolar electrosurgical instrument for use in the bulk removal of tissue, as in a laparoscopic hysterectomy.

In a laparoscopic hysterectomy, the body of the uterus is resected from the stump, and then removed from the operative site. To enable the uterus to be removed through a limited surgical opening, it is desirable to morcellate it into relatively smaller pieces of tissue, which are easier to remove. The present invention relates to an instrument and method for morcellating and removing a uterus.

U.S. Pat. Nos. 5,957,884, 6,007,512 and 6,036,681 are examples of morcellating devices in which an element carrying an electrode is rotated in order to cause the morcellation of tissue. This rotation of the electrode necessitates a mechanical drive arrangement, which increases the complexity of the instrument. The present invention seeks to provide a simpler, and hence more reliable, arrangement for the bulk removal of tissue.

BRIEF SUMMARY OF THE INVENTION

Accordingly, there is provided a morcellating system comprising an electrosurgical generator and a morcellating device for morcellating tissue within a body cavity of a patient, the morcellating device comprising a stationary tube having a distal end portion, and a bipolar electrosurgical electrode assembly comprising first and second electrodes located at the distal end of the tube and separated one from the other by an insulation member, the bipolar electrosurgical electrode assembly being connectable to the electrosurgical generator such that an electrosurgical cutting voltage can be applied to the electrode assembly, the electrosurgical generator being adapted to supply the electrosurgical cutting voltage to the electrode assembly in the form of a pulsed cutting voltage.

Surprisingly, the pulsing of the cutting voltage has been found not to interfere with the acceptable cutting performance of the morcellating system, but dramatically to reduce the smoke generated when the tissue is being morcellated.

Conveniently, the pulsed cutting voltage has a duty cycle of between 40% and 90%, typically between 60% and 80%, and preferably substantially 80%. In one convenient arrangement, the pulsed cutting voltage has a duty cycle which is substantially constant.

Alternatively or additionally, the pulsed cutting voltage has a period of between 200 ms and 1 second, conveniently between 400 ms and 600 ms, and typically substantially 500 ms. In one convenient arrangement, the pulsed cutting voltage has a period which is substantially constant.

In a preferred arrangement, one or more temperature sensors are provided to give an indication of the temperature of the distal end of the tube. The electrosurgical generator is conveniently controlled such that a parameter of the pulsed cutting voltage is dependent on the temperature of the distal end of the tube as indicated by the one or more temperature sensors. In one convenient arrangement, the parameter of the pulsed cutting voltage that is dependent on the temperature of the distal end of the tube is the duty cycle of the pulsed cutting voltage.

In one arrangement, the electrosurgical generator is controlled such that the pulsed cutting voltage has at least a minimum duty cycle (typically 40%) regardless of the temperature of the distal end of the tube as indicated by the one or more temperature sensors. Alternatively or additionally, the electrosurgical generator is controlled such that the pulsed cutting voltage has a maximum duty cycle (typically 80%) regardless of the temperature of the distal end of the tube as indicated by the one or more temperature sensors.

In an additional or alternative arrangement, the electrosurgical generator is controlled such that the cutting voltage in each pulse is terminated when the indication of the temperature of the distal end of the tube reaches a predetermined threshold. Typically, the predetermined threshold is between 70° C. and 90° C., and preferably between 80° C. and 85° C.

In one convenient arrangement, the pulsed cutting voltage has a shaped waveform, typically in the form of a generally tapered profile, reducing from a predetermined maximum voltage level. The pulsed cutting voltage may conveniently reduce from a predetermined maximum voltage level to a predetermined minimum voltage level. The voltage level required to maintain a cutting plasma around the active electrode is less than that required to initiate the cutting plasma in the first place. Thus, the voltage can be "backed off" after the initiation of the plasma, in order to reduce the temperature of the active electrode, without compromising the continued cutting capability of the instrument.

The pulsed cutting voltage is preferably maintained for a predetermined initial period at the predetermined maximum voltage level, before it starts to reduce therefrom. This ensures the effective establishing of a cutting plasma before the voltage starts to reduce.

In another convenient arrangement, the morcellating system includes means for determining whether the bipolar electrode assembly is in contact with tissue, and wherein the electrosurgical generator is controlled such that the voltage only starts to reduce once the bipolar electrode assembly is in contact with tissue. This ensures that, where the voltage signal is initiated before the electrode assembly has come into contact with tissue, the voltage signal is at a maximum when the electrodes do come into contact with the tissue. This effectively avoids the possibility that the electrode assembly is unable to produce a cutting plasma because the tapered voltage waveform is part way through its voltage reduction cycle when the electrode assembly comes into contact with tissue.

Conveniently, the electrosurgical generator is controlled such that the voltage only starts to reduce once the bipolar electrode assembly has been in contact with tissue for a predetermined period of time.

Typically the means for determining whether the bipolar electrode assembly is in contact with tissue comprises means for measuring the impedance between the first and second electrodes.

Conveniently, the electrosurgical electrode assembly extends around the circumference of the distal edge of the tube, preferably completely around the circumferential edge.

U.S. Pat. No. 5,304,124 describes an instrument for removing a myoma from the uterus of a patient, the device utilising a cauterising element at the end of a tubular member. This cauterising element is described as being a wire loop, or a "Bovie-type component". As this device is for the removal of a myoma (leaving the remainder of the uterus intact), the cauterising element will reduce the bleeding from the remainder of the uterus, which will still be vascularly connected to the patient. In contrast, the present invention provides a bipolar electrosurgical device, more suited to the bulk removal of tissue from a uterus which has been resected and will no longer have a vascular supply.

The second electrode of the bipolar assembly is preferably set back axially from the first electrode along the longitudinal axis of the tube. The tube itself conveniently constitutes the first electrode, the second electrode, or the insulating member. In one arrangement, at least one of the electrodes comprises a conductive track present on the insulating member, for example by the printing of the track on the insulating member.

The second electrode is conveniently additionally located on, or constituted by, the tissue-pulling device. With the second electrode located on the tube, if there is no electrical connection between the second electrode and the tissue-pulling device, there will possibly be a situation in which tissue being pulled into the tube is in contact with the first electrode but not the second. Under these circumstances, the electrosurgical cutting of the tissue will not be effected until the tissue is pulled far enough so as to contact the second electrode. By placing the second electrode on the tissue-pulling device, or by making the second electrode in electrical communication with the tissue-pulling device, the cutting of tissue will be effected by a bipolar electrode assembly constituted between the tissue-pulling device and the first electrode.

By providing both a second electrode on the tube, and making the tissue-pulling device effective as the second electrode, each will act as the second electrode at different times. When the tissue is first presented to the tube, the tissue-pulling device will act as the second electrode. Subsequently, as the tissue is pulled into the tube, the bipolar cutting will occur between the first electrode and the second electrode located on the tube. This arrangement ensures that, as the first tissue contact with the tube is established, the bipolar electrode assembly is capable of firing up successfully, and yet continues to be effective as more and more tissue is pulled into the tube.

Thus, it will be seen that the bipolar electrode assembly is constituted by having two electrodes in the distal region of the tube, and additionally an optional electrode on the tissue-pulling device. Either of these arrangements constitute "bipolar" electrode assemblies, even if the tissue-pulling device constitutes an additional electrode. A bipolar electrode assembly has at least two electrodes, manoeuvrable in the immediate region of the surgical site. This is in contrast to monopolar or "Bovie type" arrangements, in which an immovable return pad is attached to the patient at a point somewhat removed from the surgical site.

The tissue-pulling device is preferably longitudinally movable with respect to the tube. By the use of a pulling device, the tube can be maintained stationary and tissue pulled into the end of the tube. There is, therefore, no need to advance the tube or otherwise move it into the tissue to be removed, as with many of the prior art devices.

The tissue-pulling device is preferably a pair of jaw members movable between open and closed positions, the jaw members conveniently being mounted on a rod extending through the tube. The jaws can be closed around tissue, grasping it firmly, and the rod retracted within the tube to cause the tissue to be severed by the electrosurgical electrode assembly at the distal end of the tube. Alternatively, the tissue-pulling device comprises a screw member rotatable with respect to the tube. Rotation of the screw member has the effect of pulling tissue into the tube.

The tube conveniently has an end face which is angled with respect to the longitudinal axis of the tube, preferably at an angle of between 30 and 60 degrees to the longitudinal axis, and typically at 45 degrees thereto. This angled end face helps to ensure that the initial contact between the tissue and the electrode assembly is a point contact, thereby assisting with the firing-up of the electrode assembly into a cutting or vaporisation mode and ensuring effective separation of the tissue. The stationary tube alternatively has an end face with an undulating circumference, typically a castellated or alternatively a wave-like circumferential surface. In one convenient arrangement, the circumference undulates substantially in the form of a sine wave. These different end profiles each help to provide one or more gradually progressing point of contact, as opposed to a uniform contact over the whole of the end circumference, thereby assisting with the electrosurgical cutting of tissue.

The first electrode preferably has a distal portion including a plurality of apertures disposed around its circumference, preferably in one or more rows of apertures set back from the end of the tube. The apertures are conveniently circular holes, or alternatively elongate slots, and the apertures in one row are preferably radially offset from the apertures in an adjacent row. The apertures seek to ensure that heat is not conducted away too rapidly from the distal circumference of the first electrode, thereby keeping the active electrode at a high temperature and reducing the rate at which the remainder of the instrument increases in temperature.

BRIEF DESCRIPTION OF THE DRAWINGS

The invention will now be described in more detail, by way of example only, with reference to the accompanying drawings, in which.

DETAILED DESCRIPTION OF THE INVENTION

Figure 1:
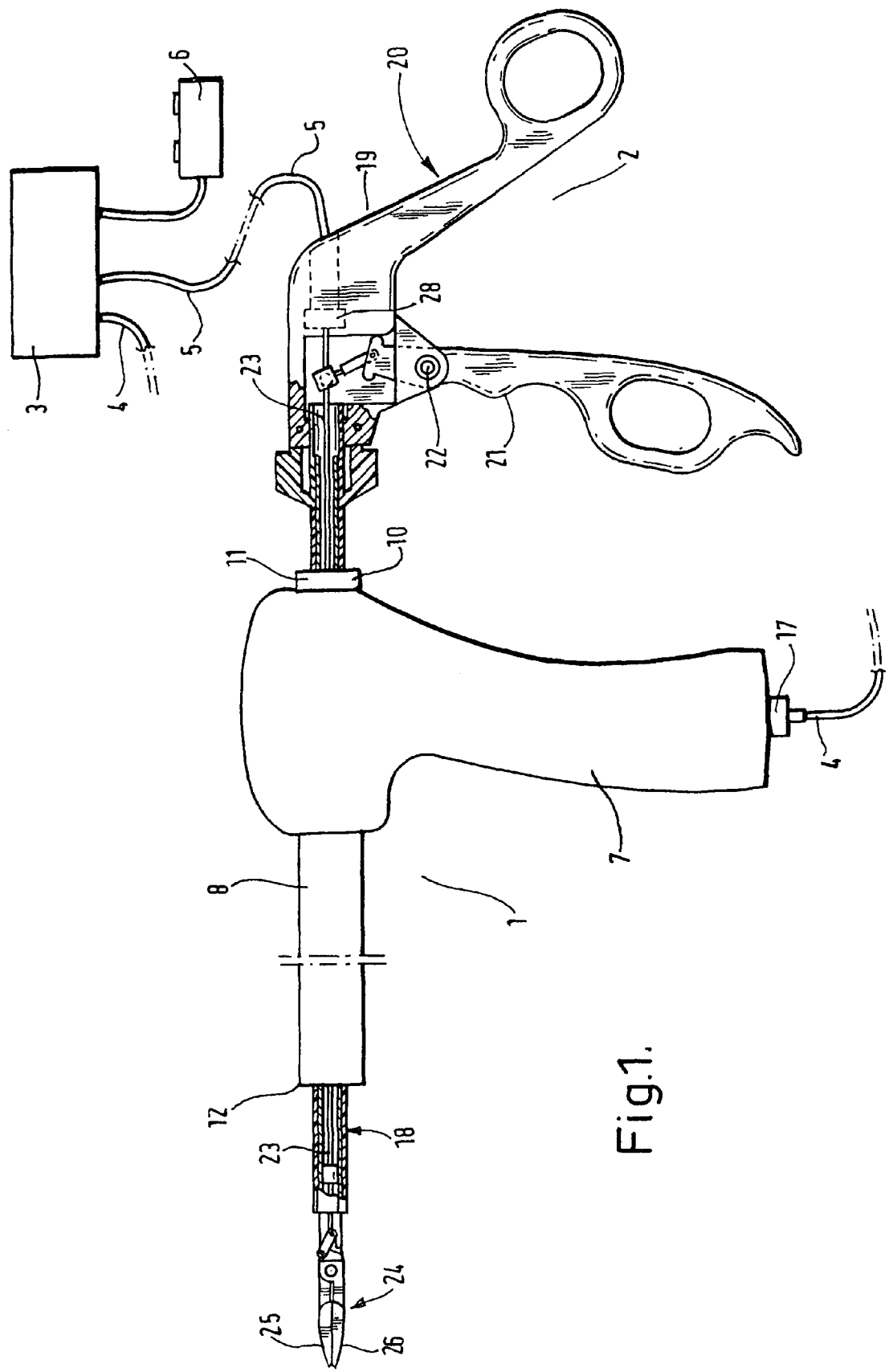
FIG. 1 is a schematic side view, partly in section, of a morcellating system constructed in accordance with the present invention.

Referring to FIG. 1, a morcellating system comprises a morcellating device shown generally at 1, a tissue-pulling device shown generally at 2, and an electrosurgical generator 3. The generator 3 is connected to the morcellating device 1 by means of a cable 4, and to a tissue grasping device by means of a cable 5. The generator 3 is controlled by means of footswitch 6.

Figure 2:
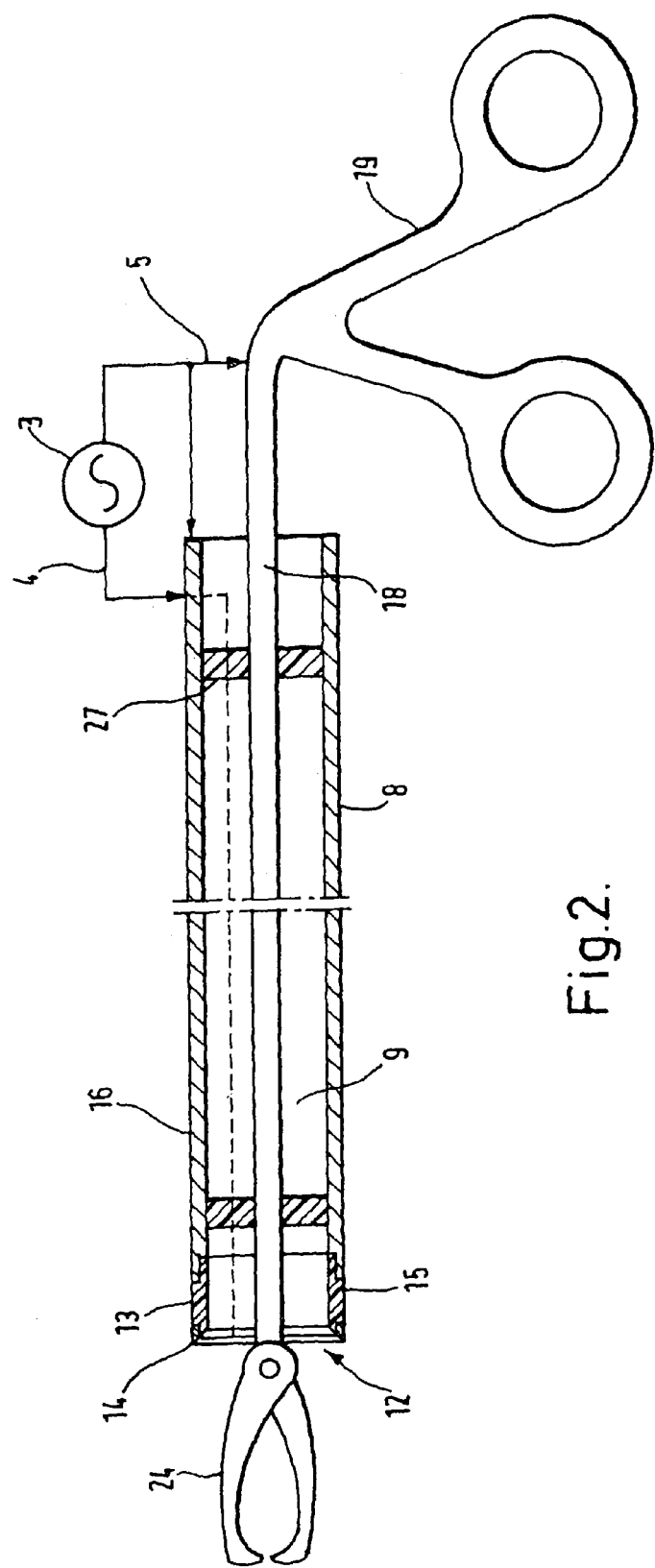
FIG. 2 is a schematic sectional view of a part of the system of FIG. 1, FIGS. 3 to 6 are schematic views of alternative embodiments of the part of FIG. 2, FIGS. 7 and 8 are schematic views of further alternative embodiment of the distal end of the part of FIG. 2, FIGS. 9 and 10 are schematic views of electrodes for use with the part of FIG. 2.

As shown in FIGS. 1 and 2, the morcellating device 1 comprises a handle 7 and a cylindrical tube 8. The cylindrical tube 8 is hollow, and defines a lumen 9 therein. The proximal end 10 of the tube 8 extends from the handle 7 as shown at 11, and the distal end 12 of the tube is provided with an electrosurgical electrode assembly 13. The electrosurgical electrode assembly 13 comprises an active tissue-cutting electrode 14, and an insulating member 15, both extending around the circumference of the tube 8. The insulating member 15 separates the electrode 14 from the remainder of the tube 8, which acts as a return electrode 16.

The tube 8 is connected to one pole of the generator 3, via the cable 4 and a connector 17. The active electrode 14 extends around the entire circumference of the tube 8, and is connected to the other pole of the generator 3, via the cable 4, the connector 17 and additional wiring (not shown). In this way, the electrodes 14 and 16 constitute a bipolar electrode assembly, which when energised by the generator 3, is capable of cutting tissue coming into contact with the distal end of the tube 12.

The tissue-pulling device 2 comprises a tubular shaft 18, at the proximal end of which is a scissors-type handle mechanism 19, with a first handle 20 and a second handle 21. The second handle 21 is pivotable with respect to the first handle 20, about a pivot pin 22. Pivoting of the second handle 21 causes longitudinal movement of a push rod 23 extending through the shaft 18 to the distal end thereof.

At the distal end of the shaft 18 is a jaw assembly 24, with a first jaw member 25 and a second jaw member 26 movable between open and closed positions by the movement of the push rod 23. The tissue-pulling device 2 is manually translatable in a longitudinal manner within the lumen 9 of the morcellating device 1, with slideable guide members 27 supporting the shaft 18 of the tissue-pulling device within the tube 8 of the morcellating device 1. The jaw members 25 and 26 are electrically connected to the shaft 18 which is electrically connected, via the cable 5 and a connector 28, with the generator 3. The shaft 18 is connected to the same pole of the generator 3 as the return electrode 16, constituted by the tube 8.

The operation of the morcellating system is as follows. The tube 8 of the morcellating device 1 is inserted into the body of a patient, typically through a trocar (not shown), and brought into position adjacent to the tissue to be removed (typically a resected uterus in the case of a laparoscopic hysterectomy). The tissue-pulling device 2 is then inserted through the lumen 9 of the morcellating device 1. The handle 21 is operated to open the jaw assembly 24, and the tissue-pulling device 2 is maneuvered so that tissue from the uterus is located between the jaw members 25 and 26. The handle 21 is then operated to close the jaw assembly 24, grasping tissue therein.

The surgeon operates the footswitch 6 to operate the generator 3 so that a pulsed electrosurgical cutting voltage is supplied between the tissue-cutting electrode 14 and the return electrode 16. As mentioned previously, the push rod 23 and the jaw assembly 24 are also electrically connected to the same pole of the generator 3 as the tube 8, and so both the tube and the jaw assembly constitute the return electrode 16. With tissue firmly grasped in the jaw assembly 24, the device 2 is slowly withdrawn from the tube 8, pulling the tissue against the distal end of the tube and the tissue-cutting electrode 14. As the tissue contacts the tissue-cutting electrode 14, it is vaporised by the pulsed electrosurgical cutting voltage, allowing the device 2 to be withdrawn further into the tube 8. In this way, a cylindrical core of tissue is formed in the tube 8, the tissue being withdrawn though the proximal end 10 of the morcellating device 1 (which remains outside the body of the patient) for disposal.

The tissue-pulling device 2 can then be re-inserted in the tube 8 such that a further core of tissue can be removed from the body of the patient. By repeating this process, large quantities of tissue can be removed from the patient in a relatively short time, such that the entire uterus can be removed, if necessary, while still employing a laparoscopic approach.

Figure 3:
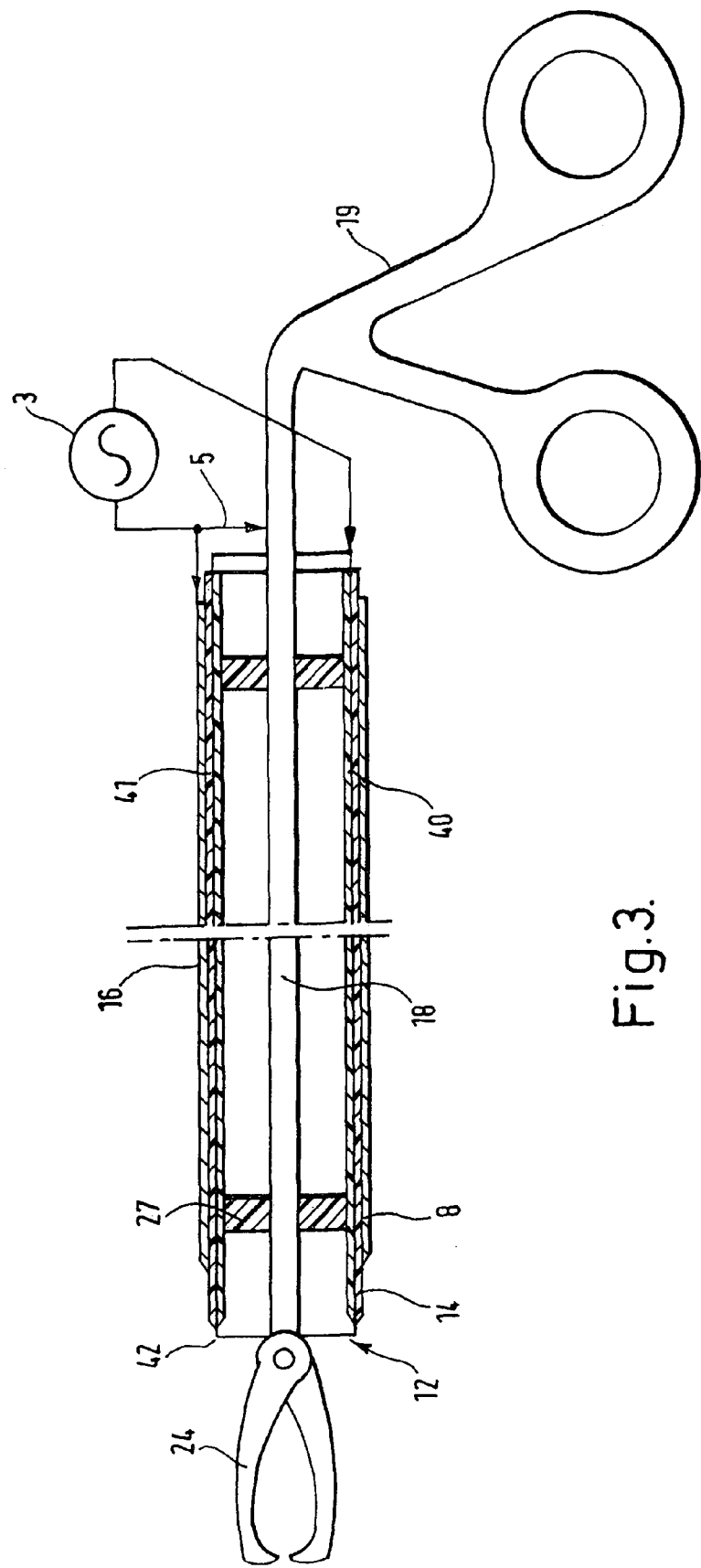

In the instrument described above, the tube 8 provides the return electrode 16 (or in other words, the return electrode provides the structural integrity of the tube). FIG. 3 shows an alternative embodiment, in which the active electrode 14 provides the structural element of the tube 8. The tube 8 is covered on its inner surface by a layer 40 of insulating material, typically a ceramic or a polymer material such as nylon or silicone rubber. The tube 8 is similarly covered on its outer surface by a layer 41, also of an insulating nylon or silicone rubber material. The insulating layers 40 and 41 stop just short of the distal end 12 of the tube 8, leaving an exposed area 42 constituting the exposed active electrode. A further deposited layer of conductive material (such as copper coated with a biocompatible material such as gold or silver) constitutes the return electrode 16.

The instrument operates in similar fashion to that described above with reference to FIGS. 1 and 2, with the tissue-pulling device 2 grasping tissue and pulling it against the distal end 12 of the tube, where it is vaporised by the pulsed current flowing between the active tissue-cutting electrode 14 and the return electrode 16.

Figure 4:
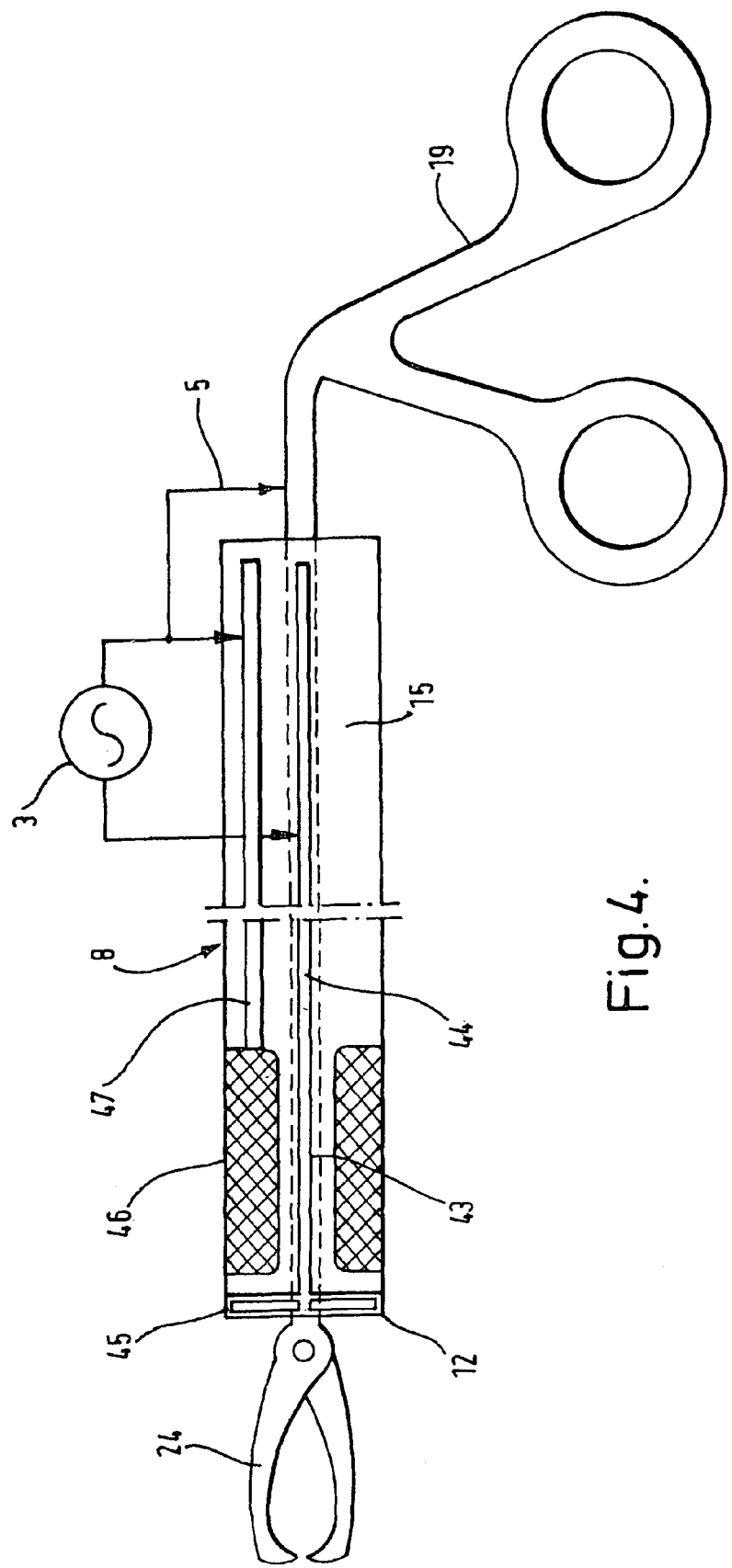

FIG. 4 shows an alternative embodiment, in which the structural integrity of the tube 8 is provided by the insulating member 15. The tube 8 is formed of a rigid ceramic or glass-reinforced nylon material, and has a metallic insert 43 attached thereto. The insert 43 has one or more longitudinal struts 44 extending the length of the tube 8. The struts 44 serve as leads for the electrosurgical current from the generator 3, and also as supports for a circumferential active electrode structure 45 at the distal end 12 of the tube. The tube 8 is also coated with a metallic material, such as copper, to form a return electrode 16. Unlike the construction shown with respect to FIG. 3, the metallic coating in the embodiment of FIG. 4 provides discrete return pads 46, and a lead 47. The return electrode structure can be provided on the inner surface of the tube 8, the outer surface, or both inner and outer surfaces.

The operation is again as previously described, with tissue being pulled against the distal end 12 of the tube 8, to be vaporised by the pulsed current flowing between the active and return electrodes.

Figure 5:
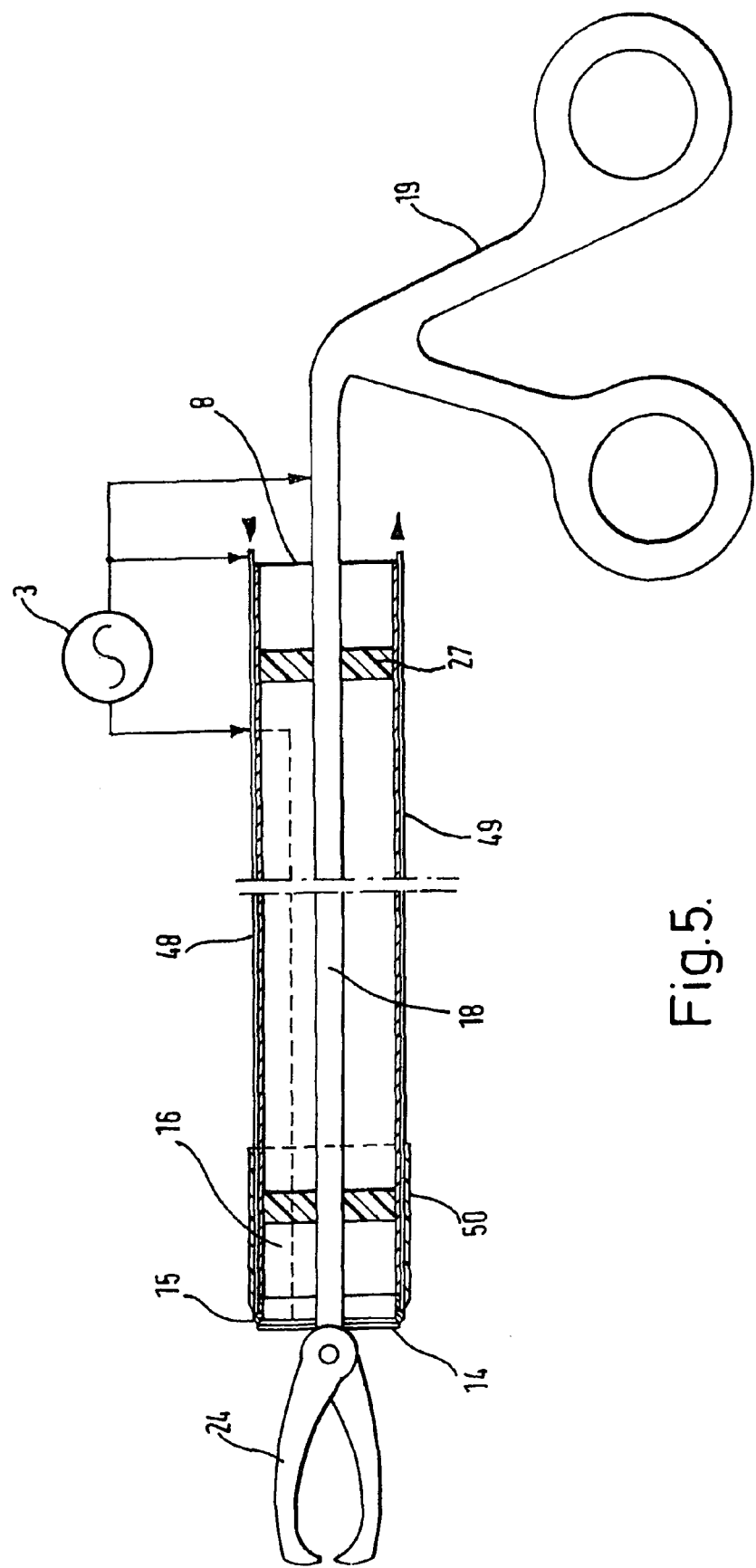

FIG. 5 shows an alternative embodiment in which a cooling system is provided to ensure that the return electrode 16 does not reach an excessive temperature. The overall construction is similar to that of FIG. 2, with previously described components being given the same reference numerals, and the return electrode 16 constituting the structural integrity of the tube 8. In addition to the tube 8, there is provided a fluid inlet pipe 48, a fluid outlet pipe 49 and a cooling jacket 50. The cooling jacket 50 surrounds the distal portion of the tube 8, while leaving the extreme distal end 12 exposed so that the active electrode 14 can contact tissue being pulled into the tube 8. Cooling fluid is pumped through the cooling jacket 50, and transfers heat away from the distal end of the return electrode 16. This ensures that the distal end of the return electrode 16 does not reach a temperature at which tissue adheres thereto.

Figure 6:
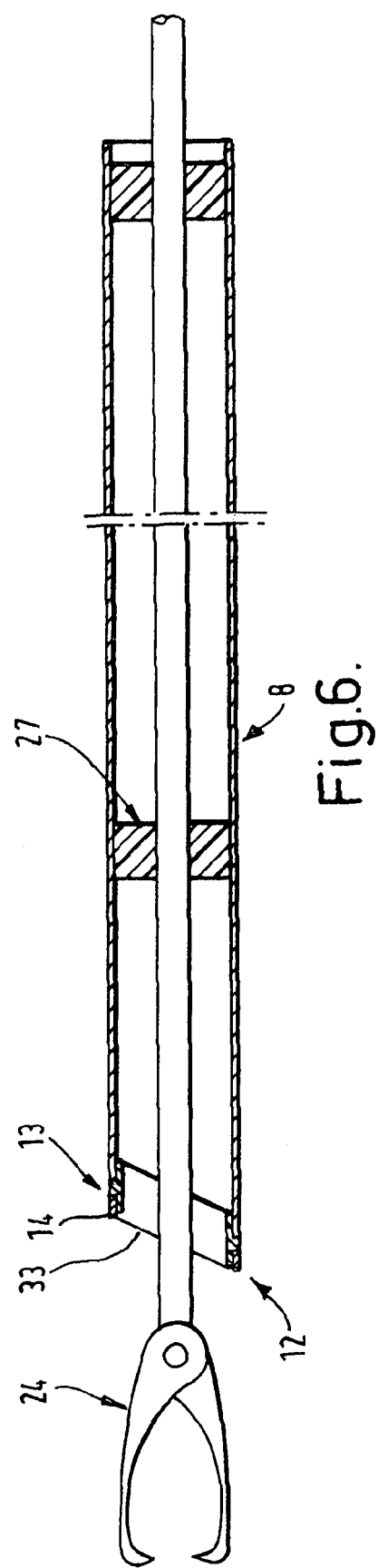

FIG. 6 shows an alternative embodiment of the tube 8, in which the distal end 12 of the tube has an angled end as shown at 33. This angled end 23, which typically lies at an angle of 45 degrees to the longitudinal axis of the tube 8, helps to provide an initial point contact between the tissue-cutting electrode 14 and the tissue being drawn into the tube. This assists in ensuring effective electrosurgical cutting of the tissue.

Figure 7:
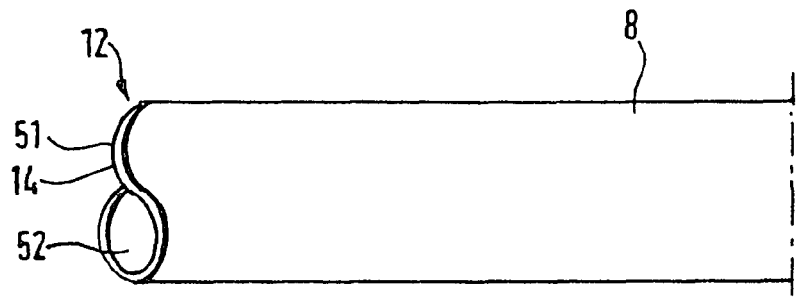

FIG. 7 shows an alternative construction in which the distal end 12 of the tube 8 has an undulating circumference. The undulating circumference is in the form of a sine wave with peaks 51 and troughs 52. Although the construction of FIG. 7 is shown with two peaks 51 and two troughs 52, constructions with other numbers of peaks and troughs are also envisaged. The undulating circumference of the end of the tube 8, which constitutes the active tissue-cutting electrode 14, ensures that the active electrode contacts the tissue at one or more point contact positions, thereby assisting in ensuring effective tissue separation.

Figure 8:
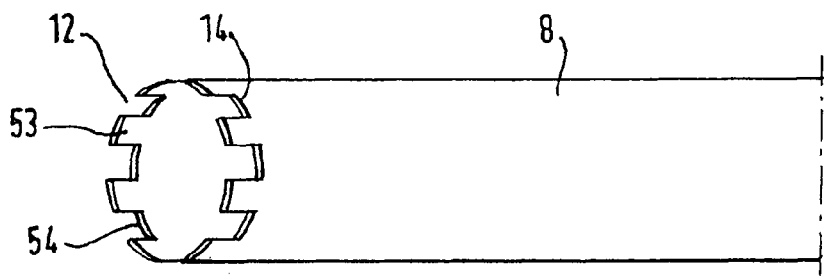

FIG. 8 shows a further embodiment of the tube in which the distal end of the tube 8 is in a castellated form, with protrusions 53 and recesses 54. Once again, this ensures that the tissue-cutting electrode 14 makes contact with the tissue at a plurality of discrete locations around the circumference of the tube.

Figure 9:
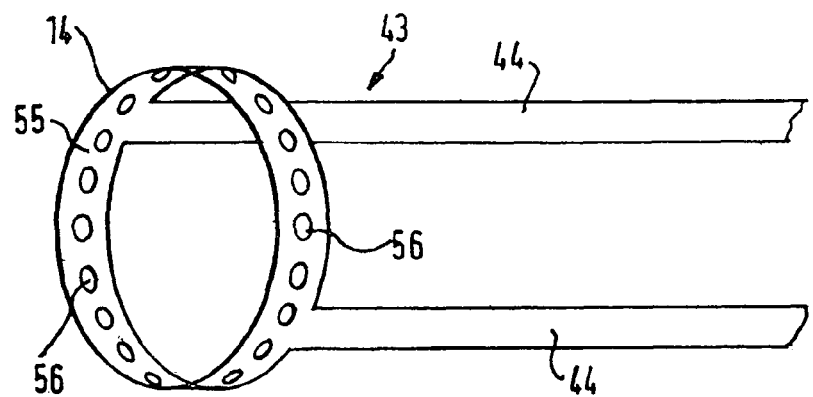

FIG. 9 shown a design of active tissue-cutting electrode 14. The electrode is in the form of a ring 55, supported by two struts 44 as previously described with reference to FIG. 4. The ring 55 is provided with a plurality of circular holes 56 extending radially around the ring. The holes 56 help to reduce the conduction of heat, generated by the tissue-cutting electrode 14, to other proximal components of the instrument, such as the insulating member 15 or the return electrode 16. This assists in maintaining the active electrode 14 at a high temperature for cutting tissue, while preventing the return electrode 16 from reaching an excessive temperature at which tissue will start to adhere to the electrode. Although the ring 55 is shown in FIG. 9 with a plain circular circumference, the holes 56 can equally be employed with the irregular-shaped constructions shown in FIGS. 7 and 8.

Figure 10:
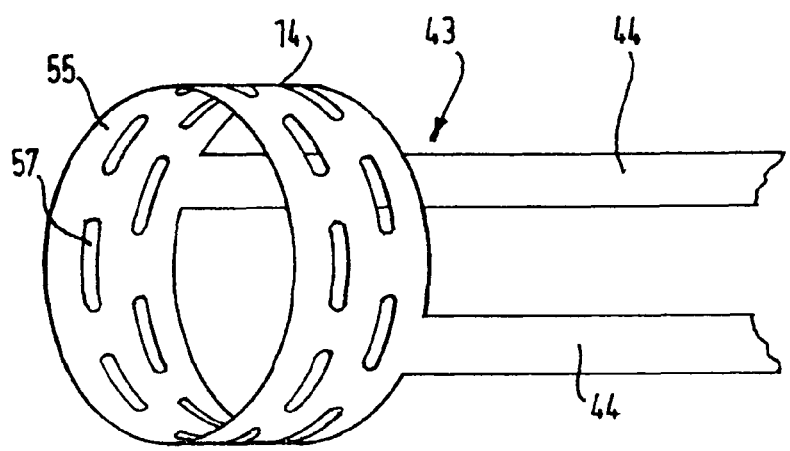

Furthermore, the holes 56 can be replaced by slots 57, as shown in FIG. 10. FIG. 10 shows an active electrode 14 in the form of a ring 55 with two staggered rows of slots 57. The staggering of the rows also helps to prevent heat generated by the active electrode 14 being passed in a proximal direction to the other components of the instrument.

Figure 11:
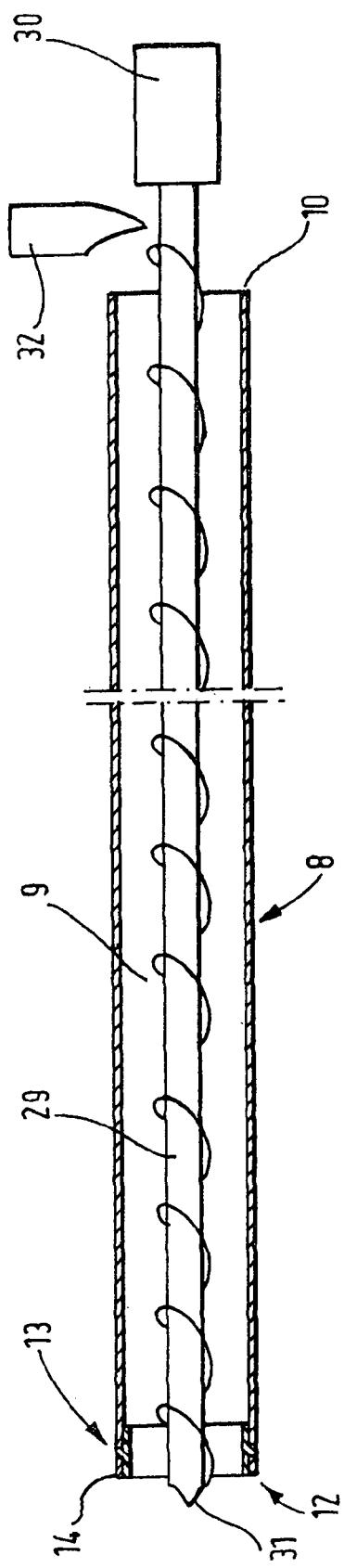
FIG. 11 is a schematic sectional view of an alternative embodiment of morcellating system constructed in accordance with the present invention.

FIG. 11 shows the tube 8 of an alternative embodiment of morcellating device 1, in which the tissue-pulling device 2 is constituted by a screw-member 29. The screw-member 29 is rotatably driven at its proximal end by means of a motor 30, and has a sharp tip 31 at its distal end. The tip 31 of the screw-member 29 engages tissue, and the rotation of the screw-member causes the tissue to be pulled against the distal end of the tube 8, where it is vaporised by the electrosurgical electrode assembly 13 as previously described. Tissue travels up the tube 8 under the action of the rotation of the screw-member 29, until it exits from the proximal end 10 of the tube, to be removed from the screw-member by a stripping element 32. This arrangement has the advantage that the extraction of tissue can be effected on an almost continuous basis, without the need for the removal and re-insertion of the tissue-pulling device of the previous Figures.

Those skilled in the art will appreciate that, in addition to the jaw device and screw-member described above, other means for pulling tissue into the tube 8 can be envisaged. The bipolar electrosurgical assembly 13 will be capable of cutting tissue pulled into contact therewith, by any suitable means.

Figure 12:
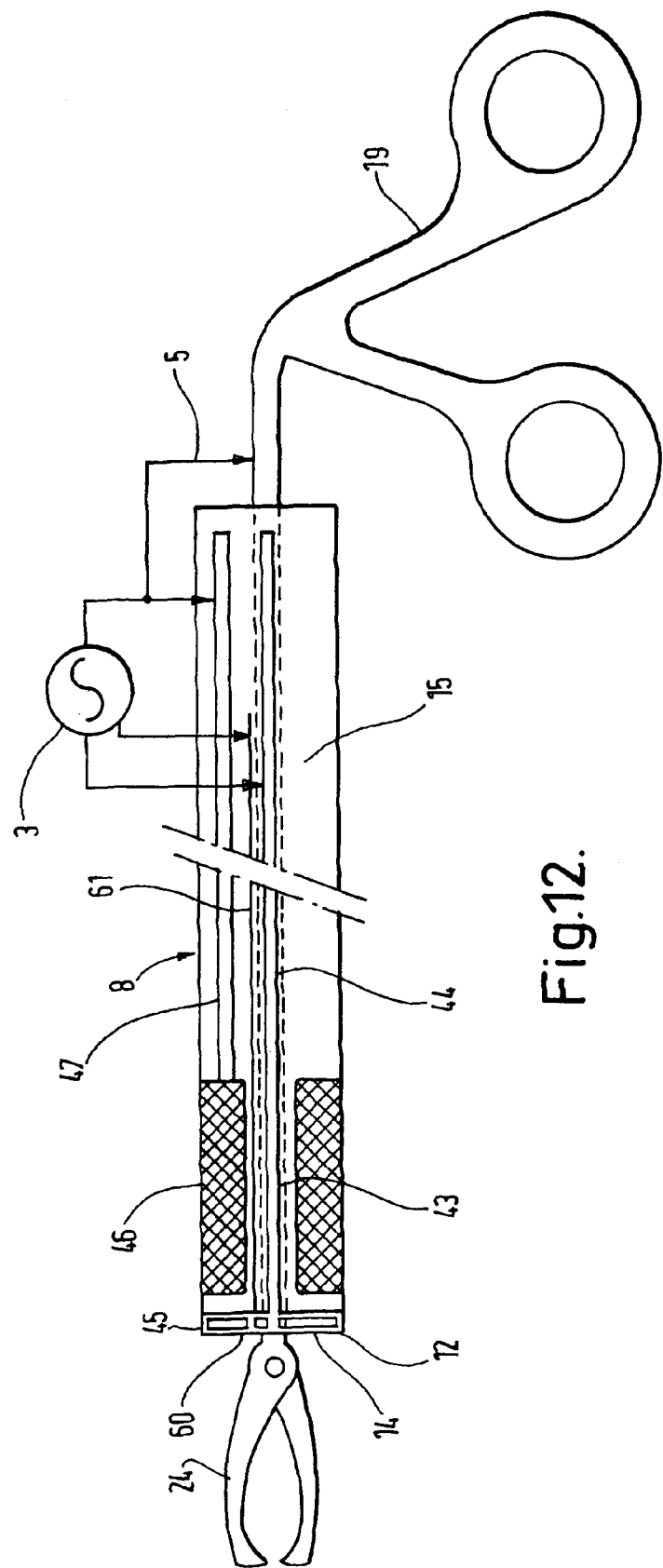
FIG. 12 is a schematic view of a morcellating device incorporating temperature sensing capabilities.

FIG. 12 shows a morcellating device including temperature sensors. The morcellating device is similar to that shown in FIG. 4, with similar features being designated with the same reference numerals as before. The temperature sensors are constituted by thermocouples 60 disposed around the active electrode 14. The thermocouples 60 are connected to the generator 3 by means of leads 61.

Figure 13A:
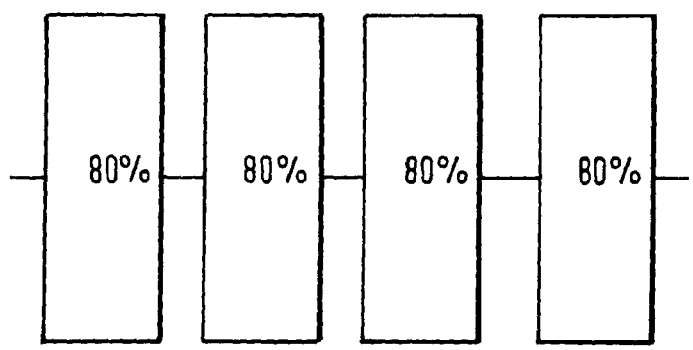
FIGS. 13A and 13B are waveform diagrams showing the pulsed delivery of energy to the morcellating device of FIG. 12.
Figure 13B:
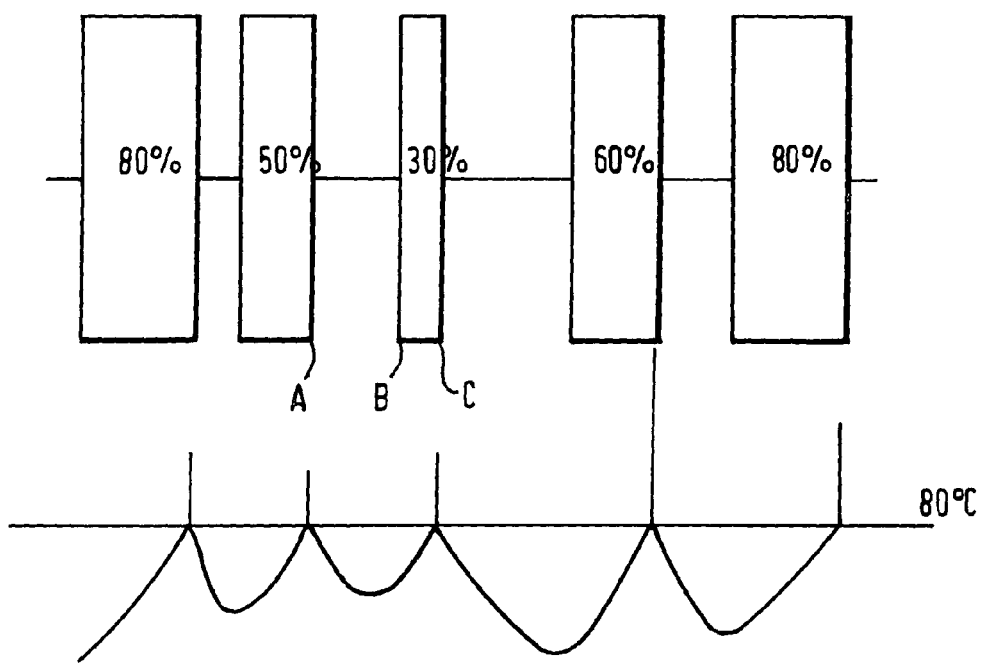

The operation of the morcellator of FIG. 12 will be further described with reference to FIGS. 13A and 13B. The generator 3 supplies a pulsed cutting voltage to the tissue-cutting electrode 14 as shown in FIG. 13A. The duty cycle of the pulsed waveform is at its permitted maximum of 80%, and has a period of 0.5 seconds. Thus the cutting voltage is "on" for 0.4 seconds, and "off" for 0.1 second. This is sufficient to reduce the smoke generated by the tissue-cutting electrode 14 when it is in contact with tissue, without compromising the effectiveness of the tissue-cutting performance.

During the operation of the morcellating device, the thermocouples 60 send temperature signals back to the generator 3. When the temperature of the tissue-cutting electrode 14 reaches a threshold temperature of 80° C., as shown at A in FIG. 13B, the pulse being delivered to the active electrode 14 is terminated, provided that it has already reached a minimum duty cycle of 20% (i.e. 0.1 second). The minimum 20% duty cycle is designed to ensure that the pulsing does not unacceptably compromise the tissue-cutting performance. In the example shown at A in FIG. 13B, the shortened duty cycle is 50%. The pulse cycle remains in its "off" condition for the remaining 50% of the pulse cycle, and then the cutting voltage is re-established as shown at B in FIG. 13B. Once again, when the temperature of the electrode 14 as measured by the thermocouples 60 reaches the 80° C. threshold, the duty cycle is shortened, this time to 30% as shown at C in FIG. 13B. This process continues with the duty cycle varying between its minimum of 20% and its maximum of 80% depending on the temperature readings as sent to the generator 3 by the thermocouples 60. This ensures that the smoke generated at the tissue-cutting electrode 14 is reduced, without affecting the tissue-cutting performance of the morcellating device.

Where intended tissue effect is plasma-based cutting, the local voltage must be high enough to initiate ionisation of the gaseous medium around the active electrode. The exact constituents of the plasma formed are dependant on the ions present; and, from the visible spectrum of emissions during electrosurgery, there would appear to be a significant proportion of sodium ions present in the generated plasma. The required peak voltage to establish a plasma is circa 300V. To sustain the plasma, there must be sufficient power dissipation local to the active electrode to counteract the cooling effects of thermal diffusion, and thus maintain temperatures above the vapour condensation point. In addition the heterogeneity of the tissue impedance may unfavourably result in higher resistivity around the return electrode, which tends to oppose the focusing of voltage and power around the active electrode. As a result of these two factors substantially higher voltages eg 480V peak, are found to be necessary to ensure more prompt creation of a cutting plasma.

Once a plasma has been established, the power density around the active electrode is at a maximum, and now the problem becomes one of continuing increases in local temperature causing excessive thermal stress of the electrode materials at or near the active electrode. In addition, the increases in tissue temperature result in greater volumes at temperatures that are able to support decomposition of hydrocarbons and greater generation of electrosurgical smoke.

Figure 14:
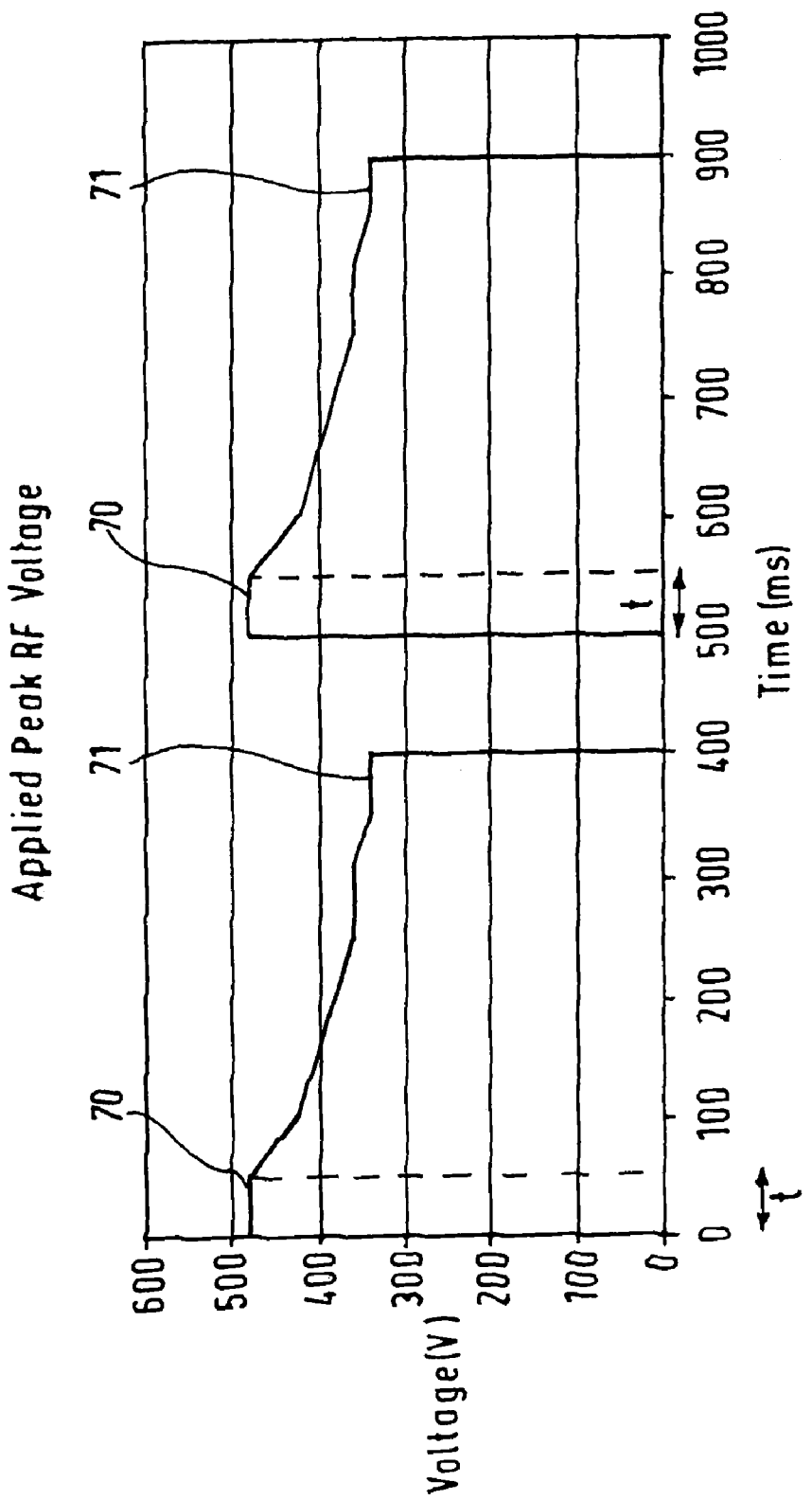
FIG. 14 is a waveform diagram of an alternative embodiment of pulsed delivery of energy to the morcellating device of FIG. 12.

FIG. 14, therefore, shows an arrangement in which the pulsed cutting voltage has a shaped waveform. In FIG. 14 a predetermined maximum voltage (480V peak) as shown at 70 is applied to tissue for a time "t" sufficient promptly to establish a plasma under a variety of tissue heterogeneity conditions. For a 42 mm diameter annular electrode, this time is found to be between 20 and 100 ms. Thereafter, the applied RF voltage is further reduced in discrete steps to a predetermined minimum value, as shown at 71, of not less than 300V peak.

In the arrangement shown in FIG. 14, the active electrode 14 of the device 1 is assumed to be in good tissue contact at the start of each 400 ms pulse of RF, and it has been found that it is advantageous to maintain the applied voltage at or near the maximum setting of 480V until the tissue impedance between the active and return electrodes is indicative of tissue contact. Where contact is detected partway through a 400 ms pulse, the voltage reduction steps are delayed, and start after a delay of 100 ms from the detection of tissue contact. Other arrangements will be apparent to those skilled in the art, for example alternative temperature control protocols, and indeed temperature sensing devices other than thermocouples are readily available. For example, the active electrode 14 can be fabricated from a resistive temperature device (RTD) material such as a platinum resistance thermometer (PRT) material. Whichever method of pulsing or temperature measurement is employed, the smoke generated by the morcellating device can be reduced or, in some cases, eliminated entirely.

The invention claimed is:

1. A morcellating system comprising an electrosurgical generator and a morcellating device for morcellating tissue within a body cavity of a patient, the morcellating device comprising a stationary tube having a distal end portion, and a bipolar electrosurgical electrode assembly comprising first and second electrodes located at the distal end of the tube and separated one from the other by an insulation member, the bipolar electrosurgical electrode assembly being connectable to the electrosurgical generator such that an electrosurgical cutting voltage can be applied to the electrode assembly, the electrosurgical generator being adapted to supply the electrosurgical cutting voltage to the electrode assembly in the form of a pulsed cutting voltage, the pulsed cutting voltage being a shaped waveform in the form of a generally tapered profile, the pulsed cutting voltage being reduced from a predetermined maximum voltage level to a predetermined minimum voltage level after the initiation of a cutting plasma around an active one of the first and second electrodes.

2. A morcellating system according to claim 1, wherein the pulsed cutting voltage has a duty cycle of between 40% and 90%.

3. A morcellating system according to claim 2, wherein the pulsed cutting voltage has a duty cycle of between 60% and 80%.

4. A morcellating system according to claim 3, wherein the pulsed cutting voltage has a duty cycle of substantially 80%.

5. A morcellating system according to claim 1, wherein the pulsed cutting voltage has a duty cycle which is substantially constant.

6. A morcellating system according to claim 1, wherein the pulsed cutting voltage has a period of between 200 ms and 1 second.

7. A morcellating system according to claim 6, wherein the pulsed cutting voltage has a period of between 400 ms and 600 ms.

8. A morcellating system according to claim 7, wherein the pulsed cutting voltage has a period of substantially 500 ms.

9. A morcellating system according to claim 6, wherein the pulsed cutting voltage has a period which is substantially constant.

10. A morcellating system according to claim 1, further comprising one or more temperature sensors to give an indication of the temperature of the distal end of the tube.

11. A morcellating system according to claim 10, wherein the electrosurgical generator is controlled such that a parameter of the pulsed cutting voltage is dependent on the temperature of the distal end of the tube as indicated by the one or more temperature sensors.

12. A morcellating system according to claim 11, wherein the parameter of the pulsed cutting voltage that is dependent on the temperature of the distal end of the tube is the duty cycle of the pulsed cutting voltage.

13. A morcellating system according to claim 12, wherein the electrosurgical generator is controlled such that the pulsed cutting voltage has at least a minimum duty cycle regardless of the temperature of the distal end of the tube as indicated by the one or more temperature sensors.

14. A morcellating system according to claim 13, wherein the electrosurgical generator is controlled such that the pulsed cutting voltage has a minimum duty cycle of 40% regardless of the temperature of the distal end of the tube as indicated by the one or more temperature sensors.

15. A morcellating system according to claim 12, wherein the electrosurgical generator is controlled such that the pulsed cutting voltage has a maximum duty cycle regardless of the temperature of the distal end of the tube as indicated by the one or more temperature sensors.

16. A morcellating system according to claim 15, wherein the electrosurgical generator is controlled such that the pulsed cutting voltage has a maximum duty cycle of 80% regardless of the temperature of the distal end of the tube as indicated by the one or more temperature sensors.

17. A morcellating system according to claim 12, wherein the electrosurgical generator is controlled such that the cutting voltage in each pulse is terminated when the indication of the temperature of the distal end of the tube reaches a predetermined threshold.

18. A morcellating system according to claim 17, wherein the electrosurgical generator is controlled such that the cutting voltage in each pulse is terminated when the indication of the temperature of the distal end of the tube reaches a predetermined threshold of between 70° C. and 90° C.

19. A morcellating system according to claim 18, wherein the electrosurgical generator is controlled such that the cutting voltage in each pulse is terminated when the indication of the temperature of the distal end of the tube reaches a predetermined threshold of between 80° C. and 85° C.

20. A morcellating system according to claim 1, wherein the first electrode extends around the circumference of the distal end of the tube.

21. A morcellating system according to claim 20, wherein the first electrode extends completely around the circumference of the stationary tube.

22. A morcellating system according to claim 1, wherein the second electrode is set back axially from the first electrode along the longitudinal axis of the tube.

23. A morcellating system according to claim 1, wherein the system is such that the pulsed cutting voltage is maintained for a predetermined initial period at the predetermined maximum voltage level, before it starts to reduce therefrom.

24. A morcellating system according to claim 1, further comprising means for determining whether the bipolar electrode assembly is in contact with tissue, and wherein the electrosurgical generator is controlled such that the voltage only starts to reduce once the bipolar electrode assembly is in contact with tissue.

25. A morcellating system according to claim 24, wherein the electrosurgical generator is controlled such that the voltage only starts to reduce once the bipolar electrode assembly has been in contact with tissue for a predetermined period of time.

26. A morcellating system according to claim 24, wherein the means for determining whether the bipolar electrode assembly is in contact with tissue comprises means for measuring the impedance between the first and second electrodes.

27. A morcellating system according to claim 1, further comprising a tissue-pulling device, the tissue-pulling device being locatable within the tube such that, when the pulsed cutting voltage is supplied to the electrode assembly, the tissue-pulling device can be moved to pull tissue against the distal end of the tube to form a core of severed tissue within the tube, and further moved in order to remove the severed tissue through the tube.

28. A morcellating system according to claim 27, wherein the second electrode is located on, or constituted by, the tissue-pulling device.

29. A morcellating system according to claim 27, wherein the tissue-pulling device is longitudinally movable with respect to the tube.

30. A morcellating system according to claim 27, wherein the tissue-pulling device comprises a pair of jaw members movable between open and closed positions.

31. A morcellating system according to claim 30, wherein the jaw members are mounted on a rod extending though the tube.

32. A morcellating system according to claim 1, wherein the voltage is reduced in steps.

33. A morcellating system according to claim 32, wherein the voltage is reduced in discrete steps.

* * * * *